United States Patent
Eifler et al.

(10) Patent No.: US 10,695,478 B2
(45) Date of Patent: Jun. 30, 2020

(54) DEVICE AND METHOD FOR SUPPLYING TREATMENT PARAMETERS FOR TREATMENT OF A PATIENT

(71) Applicant: Fresenius Medical Care Deutschland GmbH, Bad Homburg (DE)

(72) Inventors: Peter Eifler, Bad Vilbel (DE); Marco Graefe, Bad Homburg (DE); Helmut Steil, Gelnhausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1243 days.

(21) Appl. No.: 14/782,417

(22) PCT Filed: May 8, 2014

(86) PCT No.: PCT/EP2014/059448
§ 371 (c)(1),
(2) Date: Oct. 5, 2015

(87) PCT Pub. No.: WO2014/184087
PCT Pub. Date: Nov. 20, 2014

(65) Prior Publication Data
US 2016/0022892 A1      Jan. 28, 2016

(30) Foreign Application Priority Data

May 17, 2013   (DE) .................. 10 2013 008 418

(51) Int. Cl.
*A61M 1/14*    (2006.01)
*G16H 40/63*   (2018.01)
(Continued)

(52) U.S. Cl.
CPC ............ *A61M 1/14* (2013.01); *G06F 19/3481* (2013.01); *G16H 40/63* (2018.01); *G16H 50/20* (2018.01);
(Continued)

(58) Field of Classification Search
CPC .... G06Q 50/22; G06Q 50/24; G06F 19/3418; G06F 19/00; G06F 19/3468; G16H 40/67; G16H 15/00; G16H 20/17
See application file for complete search history.

(56) References Cited

U.S. PATENT DOCUMENTS

| 7,072,769 B2 | 7/2006 | Fletcher-Haynes |
| 2002/0082728 A1 | 6/2002 | Mueller et al. |

(Continued)

FOREIGN PATENT DOCUMENTS

| CN | 101189614 | 5/2008 |
| DE | 102004011264 | 9/2004 |

(Continued)

*Primary Examiner* — Joseph D Burgess
(74) *Attorney, Agent, or Firm* — Jacobson Homan, PLLC

(57) ABSTRACT

A method of supplying treatment parameters for a dialysis treatment includes supplying a predetermined machine-related data record of machine-related treatment parameters that are stipulated independently of the treatment of a specific patient, supplying a patient-related data record from patient-related treatment parameters of a patient to be treated, independently of a dialysis machine or a type of device provided for the treatment, selecting a machine-related data record for a specified dialysis treatment, and using the machine-related data record and the patient-related data record to generate a treatment data record for defining treatment parameters of the dialysis treatment to be performed.

16 Claims, 3 Drawing Sheets

(51) Int. Cl.
 *G16H 50/20* (2018.01)
 *G06F 19/00* (2018.01)
(52) U.S. Cl.
 CPC .............. *A61M 2205/3561* (2013.01); *A61M 2205/502* (2013.01)

(56) References Cited

U.S. PATENT DOCUMENTS

| | | | |
|---|---|---|---|
| 2004/0220832 | A1 | 11/2004 | Moll et al. |
| 2005/0086072 | A1 | 4/2005 | Fox, Jr. |
| 2007/0158268 | A1* | 7/2007 | DeComo ................. A61M 1/16 210/646 |
| 2010/0010425 | A1 | 1/2010 | Yu et al. |
| 2013/0310726 | A1* | 11/2013 | Miller ................. G06F 19/3481 604/5.04 |
| 2015/0355789 | A1* | 12/2015 | O'Mahony ............ G16H 20/40 715/810 |

FOREIGN PATENT DOCUMENTS

| | | |
|---|---|---|
| DE | 102005025516 | 12/2006 |
| EP | 1195708 | 4/2002 |
| WO | WO 01/65463 | 9/2001 |

* cited by examiner

DEVICE AND METHOD FOR SUPPLYING TREATMENT PARAMETERS FOR TREATMENT OF A PATIENT

BACKGROUND OF THE INVENTION

1. Field of the Invention

The present invention relates to supplying treatment parameters for treatment of a patient, in particular treatment parameters for dialysis treatment of a dialysis patient.

2. Description of Related Art

Clinic data management systems are being used to an increasing extent in everyday clinical practice. These systems are used for managing, supplying and processing patient data, treatment data, diagnostic data and other data generated or required in the treatment of patients. Dialysis clinics for care of patients who have chronic renal insufficiency are one example of the use of clinic data management systems.

Hemodialysis is a method of extracorporeal purification of the blood of patients who have chronic renal insufficiency.

In hemodialysis, blood is taken continuously from a patient in an extracorporeal circulation, passed through a hemodialyzer and reinfused back to the patient. In doing so, a mass exchange very similar to that of the kidneys is performed. The hemodialyzer consists of two chambers separated by a semipermeable membrane, one of which has blood flowing through it and the other of which has a fluid—the dialysis fluid—which is to be purified flowing through it. Commercially available hemodialyzers usually have thousands of hollow fibers for this purpose, the walls of these fibers being semipermeable for the substances to be exchanged. Blood is passed through the interior space of the hollow fibers, while the dialysis fluid is fed into the fiber interspace and removed therefrom, usually in opposite directions.

The dialysis fluid has concentrations of blood ingredients such as electrolytes, which correspond approximately to those of a healthy person, so that the corresponding concentrations can be maintained at a normal level in the blood. A time-dependent concentration profile, which is to be used for a certain treatment, may be specified for the concentration of one or more electrolytes in the dialysis fluid over the course of the treatment. Thus a concentration profile is typically stipulated for the sodium ion concentration, also referred to as the sodium profile.

Substances to be removed from the blood such as creatinine or beta-2-microglobulin, for example, are not present in the dialysis fluid, so they are removed from the blood by diffusion based solely on the concentration gradient on the membrane. Excess water is withdrawn from the blood by convection and/or by ultrafiltration with the help of a pressure gradient. A time-dependent ultrafiltration profile that is to be used for a certain treatment may be preselected for the ultrafiltration rate over the course of a treatment.

Data management systems in the field of dialysis today have a modular design and use coordinated system components to be able to cover the individual requirements and work tasks of the users. They consist of a system (monitoring system) which is connected to the dialysis machines and a system for managing patient-related data records (clinical management system). The treatment prescriptions for treatment of patients are prescribed here in the clinical management system and then used for automated presetting of the dialysis equipment using patient-specific and treatment-specific data by way of the monitoring system. In this process, the data formats of a certain dialysis machine which is intended for the dialysis treatment must be known in the clinical management system. The treatment parameters provided for a dialysis treatment must thus be coordinated with the type of machine provided for the treatment. If the type of machine provided for treatment of a certain patient changes for organizational reasons, for example, then the treatment parameters must be reconfigured.

One object of the present invention is therefore to provide a method and a system which will permit a flexible configuration of treatment parameters.

SUMMARY OF THE INVENTION

This object is achieved by a method for supplying treatment parameters for controlling or monitoring a dialysis machine, and by a system, as described herein. Advantageous embodiments of the invention are described herein.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
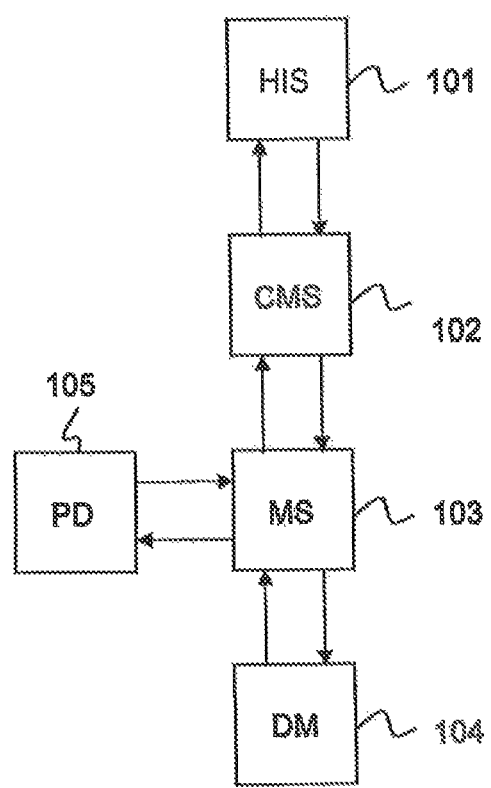
FIG. 1 shows a block diagram of a data management system in accordance with the teaching of the disclosure.

FIG. 1 shows a data management system for use in the field of dialysis. A data management system in the field of dialysis is typically associated with a hospital information system 101 for handling general patient data of dialysis patients, for example, accounting data or therapeutic or diagnostic data for the patient, without having any direct reference to the patient's dialysis treatment. The hospital information system 101 is designed for bidirectional data exchange with a clinical management system 102, for handling of patient data records that are directly related to the dialysis treatment, such as trend data, e.g., trends in data for fluid management such as dry weight, hyperhydration, iron balance, etc. This information may be used for long-term documentation, for example. The clinical management system 101 serves as an interface for the physician or other treatment person for input of treatment prescriptions, e.g., with reference to the fluid management of a patient such as the ultrafiltration profiles or weight loss profiles or the concentration profiles for the dialysis fluid to be used over the course of the treatment such as the sodium profile, the profile for the course of the sodium concentration over the time of the treatment or for other electrolyte profiles. The concepts of the treatment profile should be understood below to include the profiles based on fluid management such as ultrafiltration profiles or weight loss profiles or concentration profiles such as electrolyte profiles.

The clinical management system 102 is connected to a monitoring system for bidirectional data communication with a monitoring system 103, which monitors and controls the dialysis machines 104. The monitoring system 103 is in turn connected to peripheral devices 105 such as scales or bioimpedance measuring devices, which send test data over this connection to the monitoring system 103. The dialysis machines 104 are triggered by the monitoring system 103, so that the treatment data determined by the peripheral devices can be used.

Figure 2:
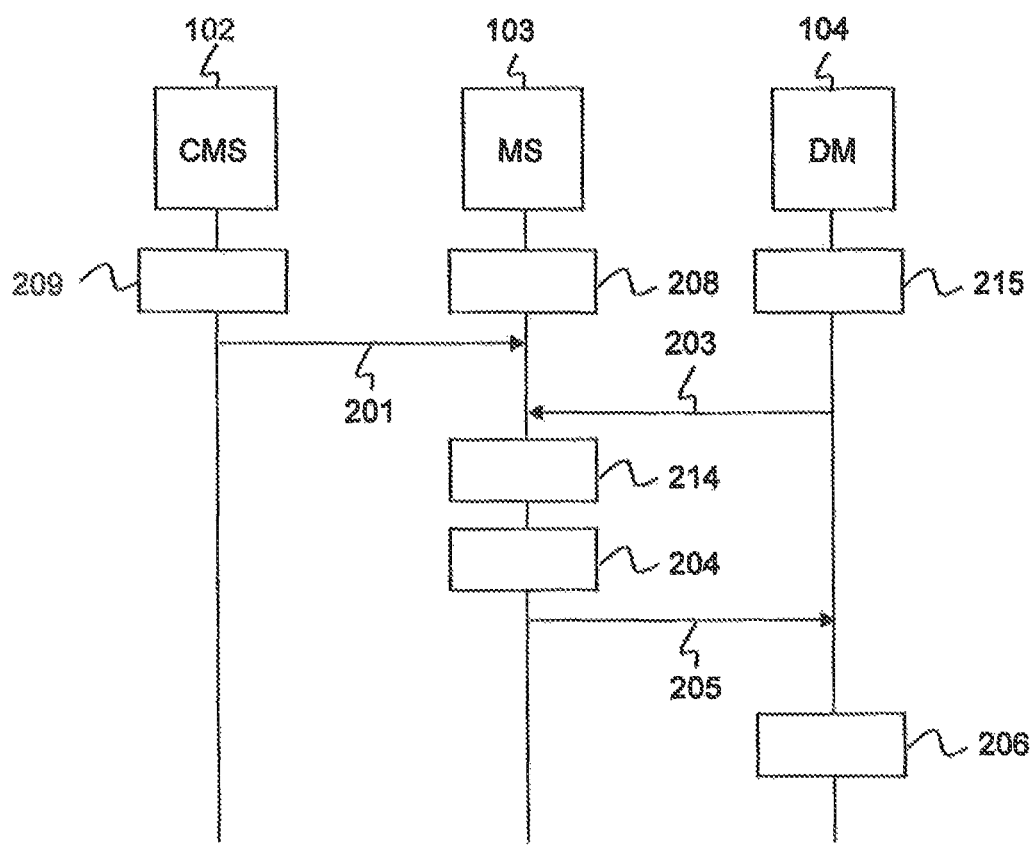
FIG. 2 shows a flow chart of a method in a data management system in accordance with the teaching of the disclosure.

FIG. 2 shows a flow chart for a flow of communications and a sequence of processing steps in conjunction with the data management system shown in FIG. 1. The elements of the data management system are shown with the same reference numerals.

The treatment is preceded by an input step 208 for input of machine-related treatment parameters which are independent of the treatment of a certain patient.

The treatment is also preceded by an input step 209 for input of a patient-related data record of patient-related treatment parameters of a patient to be treated, or in other words, the prescription for the patient to be treated. A patient-related data record, or in other words, a prescription data record, is created for the prescription. The prescription data record contains stipulations for the dialysis treatment to be performed in a form, which is independent of the dialysis machine or its type of machine. Treatment parameters for the entire treatment can thus be preselected for ultrafiltration, including, for example, the ultrafiltration rate at the start of the treatment, the ultrafiltration rate at the end of the treatment, the total ultrafiltration quantity to be withdrawn, the maximum ultrafiltration rate, the minimum ultrafiltration rate or the average ultrafiltration rate. Similarly, a treatment parameter for the entire treatment can be preselected for an electrolyte concentration, such as a sodium concentration, e.g., a sodium concentration at the start of the treatment, a sodium concentration at the end of the treatment, a maximum sodium concentration, a minimum sodium concentration or an average sodium concentration or a value of the sodium concentration that has been integrated or added up over the duration of the treatment or a total quantity.

In one embodiment the basic type of a treatment profile such as a constant profile, a rising profile, a falling profile, a step profile, a ramp profile or a comb profile, in which there is repeated switching between two different values, may also be preselected. In this way, a certain property of a treatment profile can be predetermined without already having to make a selection of the treatment profile to be used for the dialysis treatment. Thus, for example, it is possible to preselect that a rising profile is to be used when it is left open whether it should be implemented as a profile rising at a constant slope or a step profile or in which chronological sequence the steps are to be provided.

For a certain type of dialysis machine, typically a certain number of basic types of treatment profiles or basic profiles are possible.

In addition, several basic types of treatment profiles may be predetermined, such that a sequence of different priorities for the different basic types is given, for example, a profile rising at a constant rate with a first priority, a step profile rising with a second priority, etc.

The patient-related treatment data are transferred from the clinical management system 102 to the monitoring system 103 in the message 201.

In a selection step, the selection of the dialysis machine 104 provided for the dialysis treatment is made, for example, when a nurse logs a patient onto the dialysis machine provided for him. In the message 203, the dialysis machine 104 reports an identification to the monitoring system 103, allowing the type of dialysis machine 104 provided for the dialysis treatment of the patient to be determined.

On the basis of the identification of the dialysis machine, the selection of a machine-related data record for a certain dialysis treatment of the patient is made in a processing step 214.

In a processing step 204, a treatment data record for defining the treatment parameters for the dialysis treatment to be performed is compiled using the machine-related data record and the patient-related data record.

Thus, the treatment profile to be used during the treatment can be determined on the basis of the type of machine provided for the treatment, the basic type of treatment profile and the treatment parameters.

To do so, a basic profile, for example, a dimensionless or standardized profile may be formed first, for example, on the basis of the basic type of treatment profile and the type of machine, for example, on the basis of a rising profile, a step profile with a certain number of steps according to the type of machine.

Thus the treatment profile to be used for the treatment can be formed from the basis profile and the treatment parameter, e.g., by multiplying an average value times a dimensionless or standardized basic profile.

The treatment profile to be used for the treatment is tied into a treatment data record which defines the treatment parameters for the dialysis treatment to be performed. The treatment data record is sent in a message 205 to the dialysis machine which performs a dialysis treatment in a treatment step 206 using the treatment parameters, in particular the treatment profiles to be employed.

Figure 3:
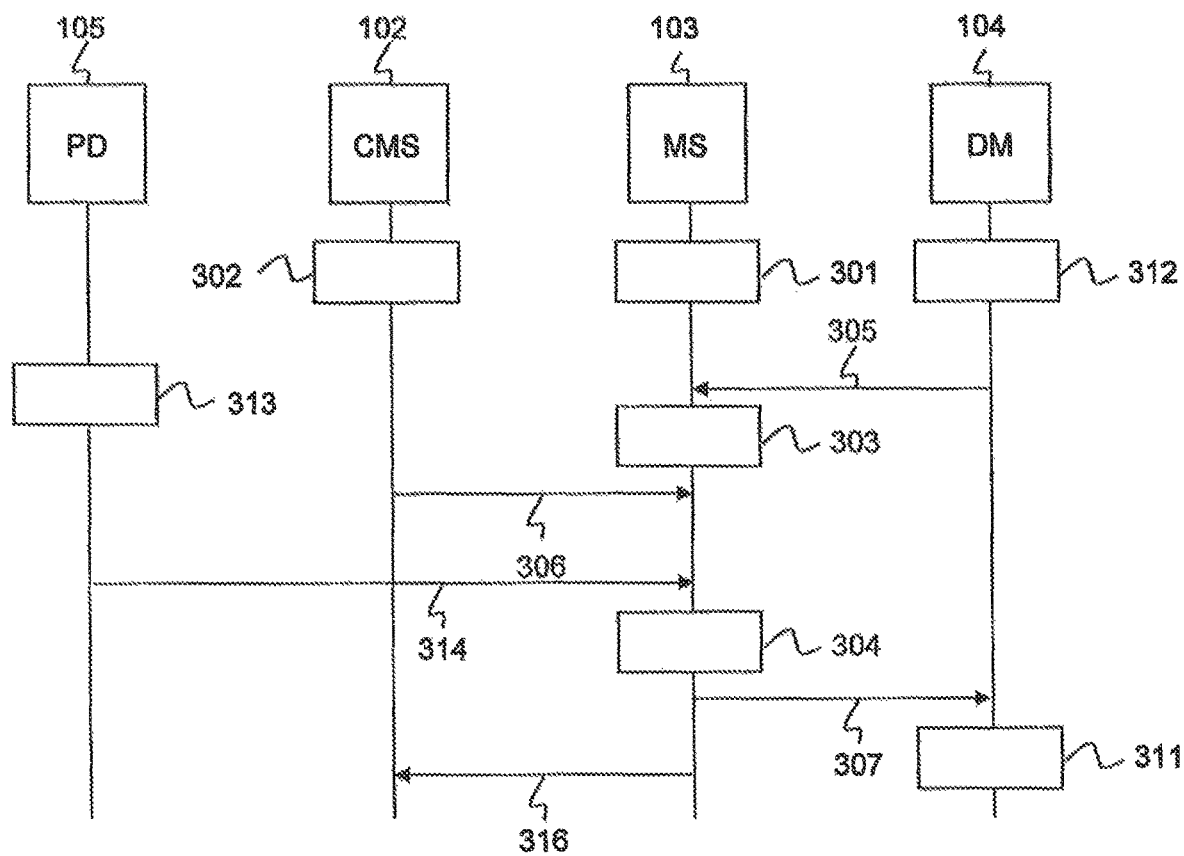
FIG. 3 shows a flow chart of another method in a data management system in accordance with the teaching of the disclosure.

FIG. 3 shows another flow chart for a flow of messages together with processing steps in conjunction with the data management system shown in FIG. 1 and with a dialysis treatment.

The dialysis treatment is preceded by a preparation step 301 for preparing for a dialysis treatment. In this step, a predetermined data record of machine-related treatment parameters is supplied in the monitoring system 103 independently of the treatment of a certain patient. Multiple data records of machine-related parameters are made available there, each for a certain type of dialysis machine, such that these parameters are stored as a function of an identification of the type of dialysis machine and they can be accessed on the basis of the type of dialysis machine.

The dialysis treatment is also preceded by another preparatory step 302, in which a patient-related data record is created in the clinical management system 102 from patient-related treatment parameters on a patient who is to be treated, independently of the dialysis machine intended for the treatment or of a certain type of dialysis machine.

The patient-related treatment parameters are preferably part of a medical prescription for the dialysis patient.

The patient-related data record preferably comprises one or more of the following elements:

the type of blood treatment method to be performed, including hemodialysis, hemofiltration, hemodiafiltration or online hemodiafiltration, specification of the weight management of the patient to be treated, including the dry weight or the target weight of the patient to be treated as well as an estimate of the weight of the clothing, a specification of the fluid management including the fluid consumption provided during the treatment to be administered, a specification for one or more medications to be administered during the treatment, a specification for anti-coagulation management to be implemented during the blood treatment, a specification for a consumable material to be used during the dialysis treatment including a type of needle to be used during the dialysis treatment, including an arterial needle, a venous needle, a type of dialyzer or tubing system to be used during the dialysis treatment, including a venous or arterial blood tubing system, a dialysis concentrate to be used during the dialysis treatment, a specification of whether the treatment is to be performed as a single-needle treatment or as multi-needle treatment (double-needle), a specification for the blood flow to be established during a hemodialysis treatment, and a treatment time provided for the dialysis treatment.

In a transmission step 306, the patient-related treatment parameters are transferred from the clinical management system to the monitoring system, where they are received.

In parallel with that, the choice of the dialysis machine 104 provided for the dialysis treatment is made in a selection step 312, for example, when a nurse logs the patient onto the respective dialysis machine, and in doing so, preferably performs an identification or authentication of the patient on the dialysis machine.

The selection step 312 is followed by the transmission of the message 305, with which the dialysis machine 104 sends an identification to the monitoring system 103, making it possible to determine the type of dialysis machine 104 provided for the dialysis treatment of the patient, such as a serial number on the dialysis machine 104, for example.

This message also preferably contains a previously determined patient identification.

The monitoring system determines the type of dialysis machine provided for the treatment on the basis of the information contained in the message 305.

On the basis of the identification of the dialysis machine, a machine-related data record of machine-related treatment parameters for a certain dialysis treatment of a patient is selected in a processing step 303.

The machine-related data record contains one or more of the following elements:

Specifications for measurements of the blood volume to be performed during the blood treatment or control of the blood volume, specifications of parameters, which may be different, depending on the type of dialysis machine, for example, an ultrafiltration profile, module settings, specifications for the measurement of recirculation or the blood temperature including the frequency of recirculation measurements or blood temperature measurements, specifications for the type of online hemodiafiltration method, i.e., whether the substituate should be added on the blood side upstream from the dialyzer (predilution), whether the substituate should be added downstream from the dialyzer (postdilution), or whether it should be added both upstream and downstream from the dialyzer (mixed dilution).

In the monitoring system 103, the patient-related treatment parameters and the machine-related treatment parameters are used to generate a treatment data record in a processing step 304, for defining treatment parameters for the individual treatment to be formed on the patient.

Furthermore, measured data from peripheral devices 313 such as scales or blood-gas analysis devices are also received in the monitoring system 103 (step 314).

These measured data are preferably taken into account in generating the treatment data record. Thus, the dry weight and the daily weight determined using the scales can be input as one of the treatment parameters in stipulating the amount of fluid to be withdrawn during a certain treatment.

The treatment data record preferably includes a control data record for controlling a dialysis machine during the dialysis treatment. The data format of the control data record conforms to the requirements of the dialysis machine provided for the treatment.

The treatment data record is preferably sent to the clinical management system (step 316) to document the documentation of the treatment performed.

The treatment data record or the control data record is sent in a transmission step 307 to the selected dialysis machine where it is received. The transmission of the control data record is preferably protected from manipulation or falsification of the data by means of an authentication mechanism or a security mechanism. In one embodiment the control data record is divided into multiple transmission packets for transmission to the dialysis machine 311.

Then the patient is treated on the dialysis machine 104 (step 311), so that the treatment data record or the control data record is used for presetting or for controlling the dialysis machine 104 during the dialysis treatment.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of supplying, with a data management system, treatment parameters for a dialysis treatment, said method comprising the steps of:

supplying a predetermined machine-related data record of machine-related treatment parameters that are stipulated independently of the dialysis treatment of a certain patient to be treated;

supplying a patient-related data record from patient-related treatment parameters of the patient to be treated, independently of a dialysis machine or of a type of device provided for the dialysis treatment;

selecting a machine-related data record for a specified dialysis treatment of the patient;

determining a type of dialysis machine to be used for the specified dialysis treatment, and selecting the machine-related data record as a function of the type of machine thereby determined; and using the machine-related data record of the determined machine and the patient-related data record to generate a treatment data record for defining treatment parameters of the dialysis treatment to be performed, the treatment data record including a control data record for controlling the dialysis machine during the dialysis treatment, with the control data record supplied to the dialysis machine being divided into a plurality of data transmission packets.

2. The method according to claim 1, wherein the step of determining the type of dialysis machine to be used for the specified dialysis treatment and selecting the machine-related data record includes supplying a plurality of the machine-related data records as a function of the type of the dialysis machine for a plurality of the types of dialysis machines.

3. The method according to claim 2, wherein the step of supplying the plurality of the machine-related data records as a function of the type of the dialysis machine is performed by a monitoring system configured to monitor a plurality of the dialysis machines.

4. The method according to claim 1, wherein the machine-related treatment parameters are a basic form of a treatment profile including a basic form of an ultrafiltration profile or a concentration profile for a dialysis fluid,
wherein the patient-related data record includes a treatment parameter that is an ultrafiltration amount or a total concentration, and
wherein the treatment data record includes the treatment profile to be used during the dialysis treatment, with the treatment profile representing the basic form of the treatment profile and the treatment parameter.

5. The method according to claim 1, wherein the machine-related treatment parameters are selected from the group consisting of specifications for measurements of blood volume, blood temperature, or circulation to be performed during the dialysis treatment, and a specification for a type of treatment of an online hemodiafiltration process.

6. The method according to claim 1, wherein the machine-related treatment parameters are selected from the group consisting of
a type of the dialysis treatment to be performed,
a specification associated with weight management of the patient to be treated,
a specification associated with fluid management during the dialysis treatment to be performed,
a specification for administration of a medication provided during the dialysis treatment,
a specification for a consumable material to be used during the dialysis treatment,
a type of dialyzer or tubing system to be used during the dialysis treatment, or a dialysis concentrate to be used during the dialysis treatment,
a specification for a blood flow rate to be set during the dialysis treatment, and
a treatment time of the dialysis treatment.

7. The method according to claim 1, wherein the patient-related treatment parameters are part of a medical prescription for the patient.

8. The method according to claim 1, wherein the step of supplying the patient-related data record from the patient-related treatment parameters includes input thereof into a clinical management system for processing patient-related information.

9. The method according to claim 3, wherein the monitoring system
receives the patient-related treatment parameters from a clinical management system,
receives an identification of the type of the dialysis machine provided for the dialysis treatment,
selects the machine-related data record based on the received identification of the type of the dialysis machine, and
supplies the control data record for controlling the dialysis machine during the dialysis treatment to the dialysis machine selected for the dialysis treatment.

10. The method according to claim 9, where the control data record is protected from manipulation by an authentication mechanism.

11. The method according to claim 1, further comprising using the supplied control data record to control the dialysis machine during the dialysis treatment.

12. A system comprising:
a clinical information system for processing patient-related information and a monitoring system for monitoring a plurality of dialysis machines and for managing a plurality of machine-related data records as a function of a respective type of machine,
the clinical information system including a memory device for supplying a patient-related data record of patient-related treatment data of a patient to be treated independently of the dialysis machine provided for the dialysis treatment, and
the monitoring system including a memory device for supplying a data record of machine-related treatment parameters which are predetermined independently of the dialysis treatment of the patient, a calculation unit, a selection device for selecting a machine-related data record for a specified dialysis treatment of the patient, a device for determining a type of dialysis machine to be used for the specified dialysis treatment, and for selecting the machine-related data record as a function of the type of machine thereby determined, and a device for using the machine-related data record and the patient-related data record to generate a treatment data record for establishing the treatment parameters of the specified dialysis treatment,
the treatment data record including a control data record for controlling the dialysis machine during the dialysis treatment, with the control data record supplied to the dialysis machine being divided into a plurality of data transmission packets.

13. The method according to claim 6, wherein the specification associated with the weight management is a dry weight or a target weight of the patient.

14. The method according to claim 6, wherein the specification associated with fluid management is a fluid intake to be provided during the dialysis treatment.

15. The method according to claim 6, wherein the specification for administration of a medication is an anticoagulant treatment to be performed during the dialysis treatment.

16. The method according to claim 6, wherein the specification for a consumable material is for a type of a needle to be used during the dialysis treatment.

* * * * *